United States Patent [19]

Okamoto et al.

[11] Patent Number: 5,736,411
[45] Date of Patent: Apr. 7, 1998

[54] CHIRAL SHIFT REAGENT FOR NMR COMPRISING SACCHARIDE DERIVATIVE

[75] Inventors: Yoshio Okamoto; Eiji Yashima, both of Aichi; Kazuma Oguni, Hyogo, all of Japan

[73] Assignee: Daicel Chemical Industries, Ltd., Osaka, Japan

[21] Appl. No.: 735,355

[22] Filed: Oct. 22, 1996

Related U.S. Application Data

[63] Continuation of Ser. No. 464,888, filed as PCT/JP94/01992, NOv. 25, 1994, abandoned.

[30] Foreign Application Priority Data

Nov. 26, 1993 [JP] Japan .................................. 5-296318
Nov. 15, 1994 [JP] Japan .................................. 6-280153

[51] Int. Cl.$^6$ ........................................ G01N 24/00
[52] U.S. Cl. ................................................ 436/173
[58] Field of Search ...................................... 436/173

[56] References Cited

U.S. PATENT DOCUMENTS 3,915,641  10/1975  Goering et al. .

FOREIGN PATENT DOCUMENTS

| 58-153164 | 9/1983 | Japan . |
| 58-153165 | 9/1983 | Japan . |
| 59-212744 | 12/1984 | Japan . |
| 63-186134 | 8/1988 | Japan . |
| 1-301156 | 12/1989 | Japan . |
| 2-259481 | 10/1990 | Japan . |
| 4-193842 | 7/1992 | Japan . |
| 91/04968 | 4/1991 | WIPO . |

OTHER PUBLICATIONS

D.D. MacNicol *Tetrahed. Lett.* 1975, 3325–3326.
D.D. MacNicol et al., *Tetrahed. Lett.* 1977, 2173–2176.
H. Asaolca *Carbohyd. Res.* 1983, 118, 302–307.
Y.Okamoto et al.*J. Chromatog.* 1986, 363, 173–186.
E. Yashima et al, *Chem. Lett.* 1994, 579–582.
K. Oguni et al. *Polym. J.* 1994, 26, 1257–1261.
K. Oguni et al. *J. Chromatog.* 1995, 694, 91–100.
B. Chankvetadze et al. *J. Chromatog.* 1994, 694, 101–109.
Y. Okamoto et al, *J. Chromatography* 1990, 513, 375–378.
S.E. Brown et al, *J. Chem. Soc. Faraday Trans.* 1991, 87, 2699–2703.
Y. Yamashoji et al. *Anal. Chim. Acta* 1492, 268, 39–47.
H.Y. Aboul–Enein et al. *Spectrosc. Lett.* 1992, 25, 1367–1383.
S.Li et al., *Anal. Chem.* 1992, 64, 1405–1412.
T.J. Wenzel et al. *J. Org. Chem.* 1992, 57, 3594–3599.
D. Fercej–Temeljotov et al. *Chirality* 1993, 5, 288–292.
Y. Kaider et al, *Bull. Chem. Soc. Japan* 1993, 66, 2225–2232.
G. Uccello–Barretta et al. *J. Org. Chem.* 1994, 59, 836–839.
S.K. Branch et al. *J. Pharm. Biomed. Anal.* 1994, 12, 1507–1517.
TrAC: Trends in Analytical Chemistry, 12 (1993) Apr., No. 4, Amsterdam, NL, pp. 185–189, A.F. Casy, "Chiral Discrimination by NMR Spectroscopy".
Magnetic Resonance in Medicine, vol. 17, No. 2, Feb. 1991, Duluth, MN pp. 516–532, S.W.A. Bligh et al., "Use of Paramagnetic Chelated Metal Derivatives of Polysaccharides and ..."
J. Am Chem. Soc., vol. 93, pp. 5913–5914 (1971) H.L. Goering et al.
J. Org. Chem., vol. 41, pp. 62–65 (1976) D. Valentine, Jr. et al.
J. Pharm. Sci., vol. 65, pp. 592–594 (1976) P. Reisberg et al.
J. Forensic Sci., vol. 24, pp. 303–306 (1976) J.A. Kroll.
Tetrahedron Letters, vol. 21, pp. 2579–2582 (1968) W.H. Pirkle et al.
Tetrahedron Letters, vol. 56, pp. 5849–5852 (1968) W.H. Pirkle et al.
J. Am. Chem. Soc., vol. 88, p. 1837 (1966) W. H. Pirkle.
J. Am Chem. Soc., vol. 88, p. 4294 (1966) T.G. Burlingame et al.
J. Am. Chem. Soc., vol. 91, pp. 5150–5155 (1969) W.H. Pirkle et al.
J. Magn. Resonance, vol. 10, pp. 95–97 (1973) R.R. Fraser et al.

*Primary Examiner*—Alen Soderquist
*Attorney, Agent, or Firm*—Flynn, Thiel, Boutell & Tanis, P.C.

[57] ABSTRACT

A chiral shift reagent for $^1$H-NMR and $^{13}$C-NMR, starting materials are easily available, synthesis is easy and of which performance is excellent, is provided. A chiral shift reagent for NMR comprising a saccharide derivative, and an analytical method which comprises measuring an NMR spectrum of an optical isomer mixture or an optically active substance in the presence of such a chiral shift reagent to analyze the mixing ratio of the optical isomers or the optical purity and absolute configuration of the optically active substance on the basis of the spectrum.

14 Claims, 8 Drawing Sheets

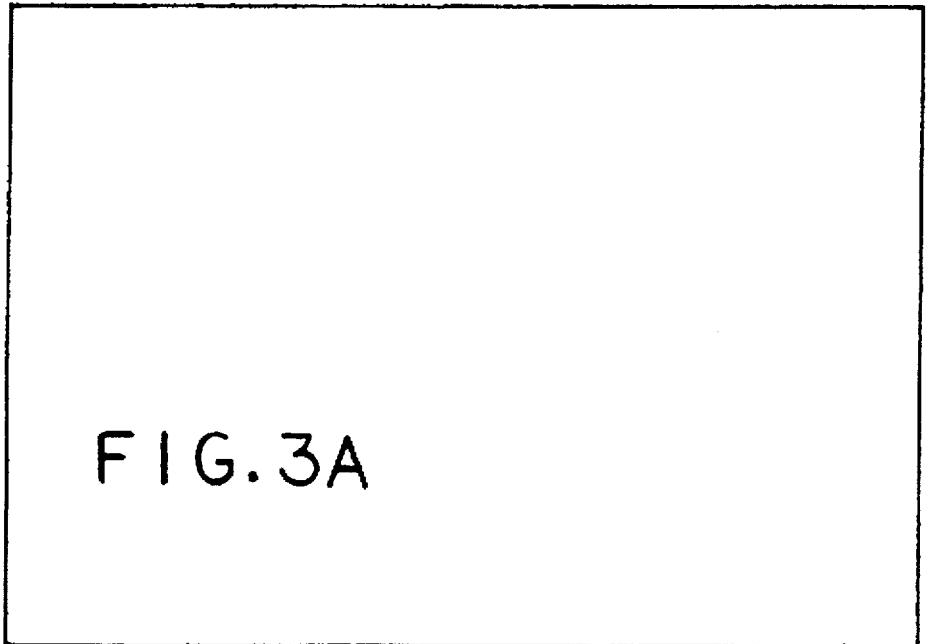
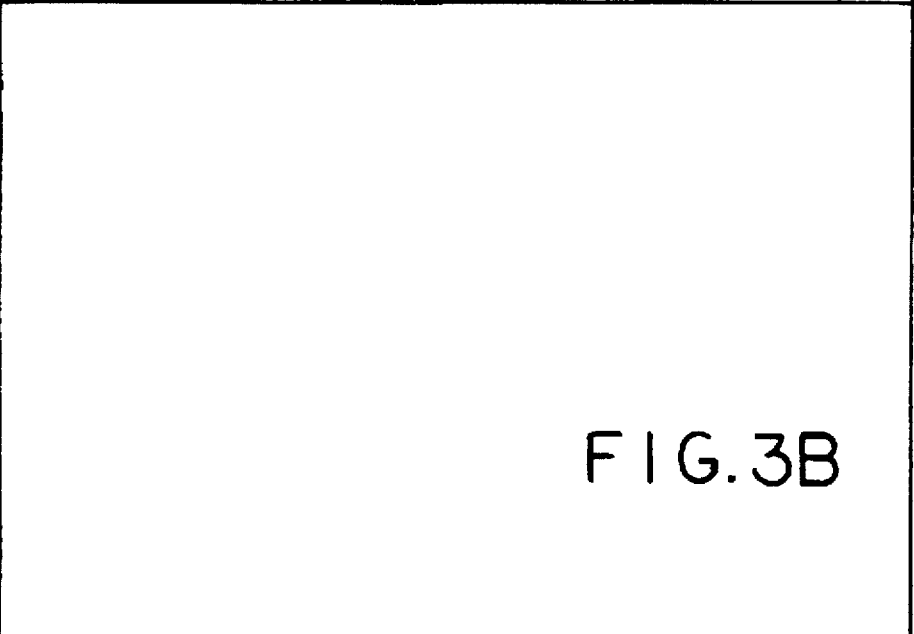
FIG. 3

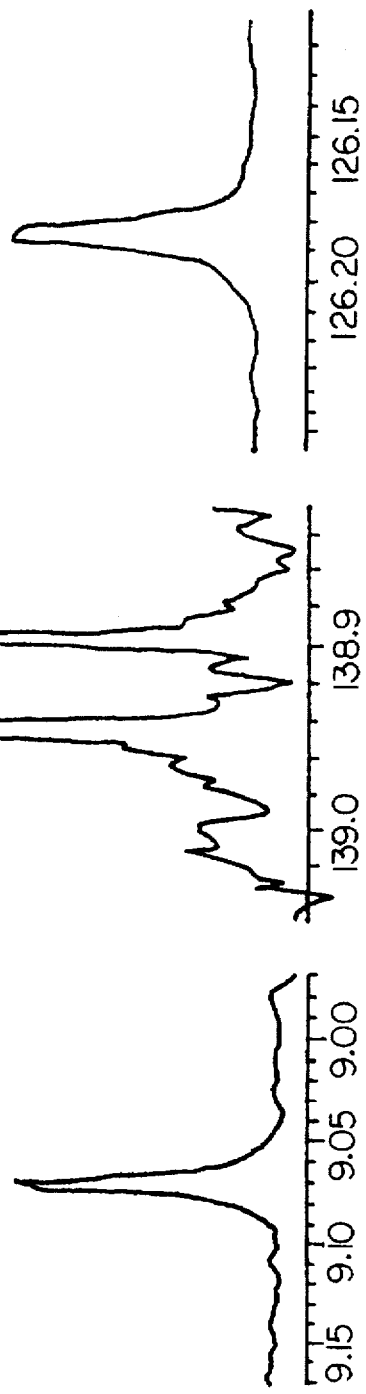
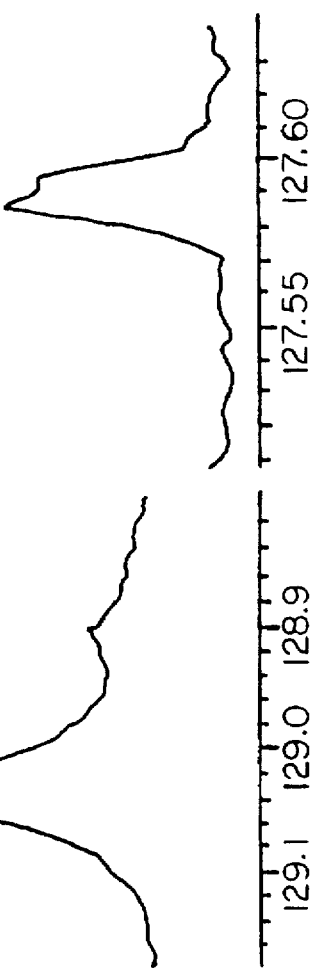
FIG. 3B

CHIRAL SHIFT REAGENT FOR NMR COMPRISING SACCHARIDE DERIVATIVE

This application is a continuation of U.S. application Ser. No. 08/464,888, filed Jun. 9, 1995, now abandoned, which is a National Stage Application from PCT/JP94/01992 filed Nov. 25, 1994.

FIELD OF INDUSTRIAL APPLICATION

The present invention relates to an optically active shift reagent (chiral shift reagent) used for analyzing an enantiometric mixture by separating signals assignable to the enantiomers of a compound having an asymmetric carbon atom in nuclear magnetic resonance spectrometry (hereinafter referred to as NMR). In particular, the present invention relates to a chiral shift reagent for NMR comprising a saccharide derivative, and a process for analyzing the mixing ratio of optical isomers in an optical isomer mixture or the optical purity and absolute configuration of an optically active substance with the chiral shift reagent.

PRIOR ART

Although optically active compounds are generally useful as pharmaceuticals, agricultural chemicals and flavors, or starting materials of them, the effect of one isomer on a living body is usually different from that of the other. Therefore, it has become very important to separate and quantify the optical isomers for improving the medicinal effect per unit dose and for the prevention of side effects and chemical injury.

Although lanthanide chiral shift reagents are well known as one to be used in the method for analyzing optically active substances by NMR (H. L. Goering et al., J. Am. Chem. Soc., 93, 5913(1971); D. Valentine et al., J. Org. Chem., 41, 62(1978); P. Reisberg et al., J. Pharm. Sci., 65, 592(1976); J. A. Kroll, J. Forenesic Sci., 24 303(1976); and others), these shift reagents have the disadvantage of being incapable of generalized use because it is difficult to synthesize or handle them, they are expensive and apt to be decompose in the presence of moisture or the like, and it is difficult to handle them.

On the other hand, in the analysis of optically active compounds, W. H. Pirkle et al. have used an optically active aromatic amine as a chiral solvent (W. H. Pirkle, J. Am. Chem. Soc., 88, 1837(1966); T. G. Burlingame et al., J. Am. Chem. Soc., 88, 4294(1968); W. H. Pirkle et al., Tetrahedron Letters, 2579(1968); and others), and have analyzed optically active compounds. Further, similarly, one example wherein amines and ester derivatives of amino acids are analyzed with optically active 2,2,2-trifluorophenylethanol as a chiral solvent, and the like have been known (W. H. Pirkle et al., Tetrahedron Letters, 5489(1968); W. H. Pirkle et al., J. Am. Chem. Soc., 91, 5150(1969); and others). However, these chiral solvents usually have such a defect that their abilities of separating the signals assignable to the optical isomers is poor.

While, although Toda et al. have disclosed a method for analyzing optically active substances with an optically active biphenyl derivative as the chiral shift reagent in Japanese Patent Publication-A No. 4-193842, this method is employable in only a limited range of application and it is difficult to apply it for generalized use.

The above-described chiral shift reagents were each developed as a reagent for analyzing optical isomers by shifting the resonance signals in $^1$H-NMR, whereas only a few reports were made on chiral shift reagents for $^{13}$C-NMR. For example, although R. R. Fraser et al. have reported tris[3-heptafluoropropyl-hydroymethylene-d-camphorato]praseodymium or tris[3-heptafluoropropylhydroxymethylene-d-camphorato]-europium which are lanthanide chiral shift reagents, similar to those for $^1$H-NMR (R. R. Fraser et al., J. Magn. Resonance, 10, 95–97(1973)), it is difficult to use these compounds because of the hygroscopicity thereof, like those described above.

DISCLOSURE OF THE PRESENT INVENTION

Under these circumstances, the present inventors have made extensive studies for the development of a chiral shift reagent for $^1$H-NMR and $^{13}$C-NMR, of which starting materials are easily available, synthesis is easy and performance is excellent. As a result, they have found that saccharide derivatives exhibit the effects as chiral shift reagents, thus completing the present invention.

Thus, the present invention provides a chiral shift reagent for NMR comprising a saccharide derivative and an analytical method characterized by measuring an NMR spectrum of an optical isomer mixture or an optically active substance in the presence of such a chiral shift reagent to analyze the mixing ratio of the optical isomers or the optical purity and absolute configuration of the optically active substance on the basis of the spectrum. More specifically, it is a method for analyzing the mixing ratio of optical isomers in an optical isomer mixture or the optical purity and absolute configuration of an optically active substance, characterized by measuring an NMR spectrum of the optical isomer mixture or the optically active substance in the presence of a chiral shift reagent for NMR comprising a saccharide derivative to analyze the mixing ratio of the optical isomers or the optical purity and absolute configuration of the optically active substance on the basis of the spectrum. The saccharide of the saccharide derivative is preferably a monosaccharide, an oligosaccharide or a polysaccharide. The saccharide derivative is preferably one obtained by substituting at least one group from those consisting of an alkyl group, an aryl group, a nitro group, an alkenyl group, an acyl group and a carbamoyl group for a part or all of the hydrogen atom(s) of the hydroxyl groups or amino groups of a saccharide. Further, the present invention is a utilization of a saccharide derivative for the above-described use.

A detailed description will now be made on the present invention.

Saccharides

The saccharide STET the saccharide derivative to be used in the present invention may be any mono-saccharide, nigosaccharide or polysaccharide, so far as it is optically active. Further, as for the chemical structure of the monosaccharide, the compound may have a ring in its molecule. Furthermore, as for the oligosaccharide and polysaccharide, the compound may be linear or cyclic. As examples of these saccharides, allose, altrose, galactose, glucose, mannose, talose, xylose and the like are cited for monosaccharides; sucrose, lactose, maltose, cellobiose, isomaltose, chitobiose, mannoblose, xylobiose, cyclodextrin, cellooligosaccharides (degree of polymerization of glucose 2 to 8), maltooligosaccharides (degree of polymerization of glucose 2 to 8) and the like for oligosaccharides; and β-1,4-glucan (cellulose), α-1,4-glucans (amylose and amylopectin), α-1,6-glucan (dextran), β-1,6-glucan, β-1,3-glucan, α-1,3-glucan, β-1,2-glucan, β-1,4-galactan, β-1,4-mannan, α-1,6-mannan, β-1,2-fructan, β-2,6-fructan, β-1,6-glucan, β-1,3-glucan, α-1,3-glucan, β-1,2- glucan, β-1,4-galactan, β-1,4-xylan, β-1,3-xylan, β-1,4-chitosan, β-1,4-acetylchitosan (chitin), pullulan, agarose, alginic acid and the like for polysaccharides. The upper limit of the average degree of polymerization of these polysaccharides is 1000, and it is preferred that the average degree of polymerization thereof be 500 or below for the measurement of the NMR spectrum.

Saccharide derivatives

The saccharide derivatives to be used in the present invention include those obtained by substituting an alkyl group, an aryl group, a nitro group, an alkenyl group, an acyl group, a carbamoyl group or the like for a part or all of the hydrogen atom(s) of the hydroxyl groups or amino groups of the saccharides exemplified above. Particular examples of the atomic groups which are introduced into the saccharides include compounds which form, by reacting them with the hydroxyl group or amino group of the saccharide, an ester bond, an urethane bond, an ether bond, an amide bond, an urea bond, an imino bond and the like which are represented by the following formulae (1) to (7).

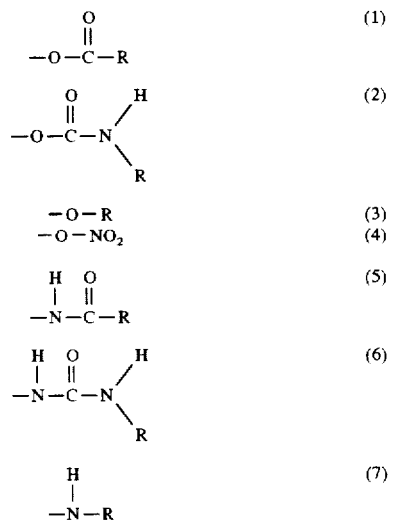

In the above formulae (1) to (7), R represents a group of which constituent carbon atom number(s) is(are) 1 to 30, which may have an unsaturated bond. Alternatively, R may represent a phenyl group represented by the following formula (8).

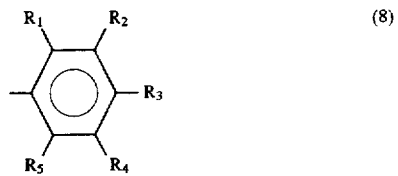

In the above formula (8), $R_1$ through $R_5$ each represents a hydrogen atom, an alkyl or alkylsilyl group having 1 to 5 carbon atoms, a halogen atom or a nitro group.

The degree of substitution for all the hydrogen atoms in the hydroxyl groups and amino groups of the saccharide derivative of the present invention is preferably 40 to 100%, still more preferably 80% or above.

The saccharides are easily available, since they occur in a large amount in nature. The ester or amide derivatives of the saccharides can be easily synthesized by reacting the saccharide with a carboxylic acid chloride corresponding to the group represented by the above formulae (1) or (8) in a suitable solvent at a high temperature. The carbamate or urea derivatives of the saccharides can be obtained by reacting the saccharide with an isocyanate corresponding to the group represented by the above formulae (2) or (6) in a suitable solvent. The imine or ether derivatives of the saccharides can be easily synthesized by reacting the saccharide with a halide corresponding to the group represented by the above formulae (3) or (7) under heating in a suitable solvent. Further, nitric esters of the saccharides can also be easily obtained by reacting the saccharide with nitric acid at a high temperature.

Method for use as chiral shift reagent

When the chiral shift reagent of the present invention comprising a saccharide derivative is used in the method for analyzing the mixing ratio of optical isomers in an optical isomer mixture or the optical purity and absolute configuration of an optically active substance, the compound to be analyzed is dissolved in a suitable solvent and a suitable amount of the chiral shift reagent of the present invention is added thereto, followed by the measurement of the NMR spectrum. When the NMR spectrum of the compound, which is the object of the analysis, is measured in such a manner, the one peak, which is observed when the chiral shift reagent of the present invention is not added, is split into two peaks in many compounds. Each of the two peaks observed in the NMR corresponds to each of the optical isomers, and the optical purity can be calculated based on the integrated intensity thereof. Further, it is also possible to empirically relate the positions of the peaks to the structures (the absolute configurations) of the optical isomers.

The chiral shift reagent of the present invention is usable for both $^1$-NMR and $^{13}$C-NMR.

EXAMPLES

The present invention will be illustrated hereinafter by referring to the Examples in greater detail. However, it is needless to say that the present invention is not limited to them.

Example 1

26 mg of racemic 1-indanol represented by the following formula (9) was mixed with 100 mg of cellulose tris(p-methylbenzoate) having glucopyranose units equimolar to the 1-indanol (hereinafter abbreviated to chiral shift reagent (1)). The mixture was dissolved in about 1.0 g of chloroform-d. As a result of the measurement (with JEOL JNM A-500) of the $^{13}$C-NMR spectra at −35° C., the chemical shift given in Table 1 was obtained. For comparison, the chemical shift of 1-indanol as measured in the absence of the chiral shift reagent (1) at −35° C. is given in the brackets.

TABLE 1

(9)

[Structure of indanol with numbered positions: OH on C1, benzene ring fused with positions 4-9, CH2 groups at 2,3]

| Position of carbon atom | Chemical shift (ppm) | Position of carbon atom | Chemical shift (ppm) |
|---|---|---|---|
| 1 | 76.15 [76.18] | 6 | 128.12 [128.15] |
|   |               |   | 128.15 |
| 2 | 35.77 [35.72] | 7 | 126.85 [126.58] |
|   | 35.81 |   |   |
| 3 | 29.64 [29.74] | 8 | 124.10 [124.24] |
| 4 | 143.22 [143.23] | 9 | 144.85 [145.03] |
|   | 143.24 |   | 144.88 |
| 5 | 124.85 [124.77] |   |   |

Figure 1:
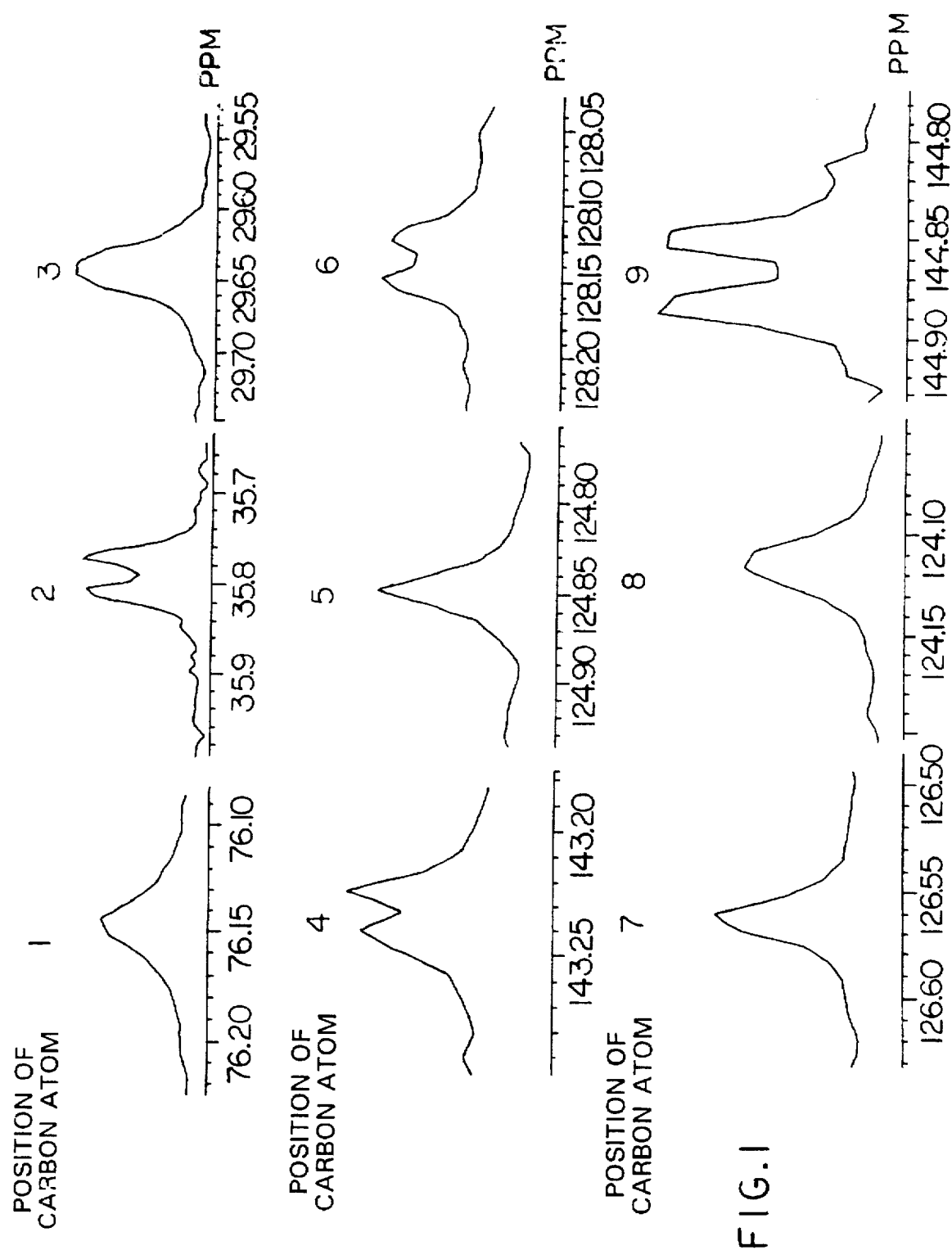
FIG. 1 is a drawing of the $^{13}$C-NMR spectra measured in the presence of the chiral shift reagent in Example 1.

The actual splittings of the $^{13}$C-NMR spectra are shown in FIG. 1.

Example 2

Optical isomers of 1-phenylethanol (R isomer and S isomer) represented by the following formula (10) were mixed with the chiral shift reagent (1) in a molar ratio of 2:1:1 (48 mg: 24 mg: 100 mg by weight ratio). About 1.0 g of chloroform-d was added thereto. As a result of the $^{13}$C-NMR measurement at 35° C., similar to Example 1, the chemical shift given in Table 2 was obtained. The assignments of R isomer and S isomer of 1-phenylethanol in the respective peaks are shown. For comparison, the chemical shift of 1-phenylethanol as measured in the absence of the chiral shift reagent (1) at 35° C. is given in the brackets.

TABLE 2

(10)

[Structure of 1-phenylethanol with OH on C1, methyl C2, phenyl ring positions 1'-6']

| Position of carbon atom | Chemical shift (ppm) |
|---|---|
| 1 | 70.214 (R) [70.11] |
|   | 70.224 (S) |
| 2 | 25.178 (S) [25.06] |
|   | 25.184 (R) |
| 1' | 145.990 (S) [145.92] |
|   | 146.009 (R) |
| 2', 6' | 125.436 [125.42] |
| 3', 5' | 128.441 (R) [128.36] |
|   | 128.444 (S) |
| 4' | 127.337 (R) [127.26] |
|   | 127.348 (S) |

Figure 2:
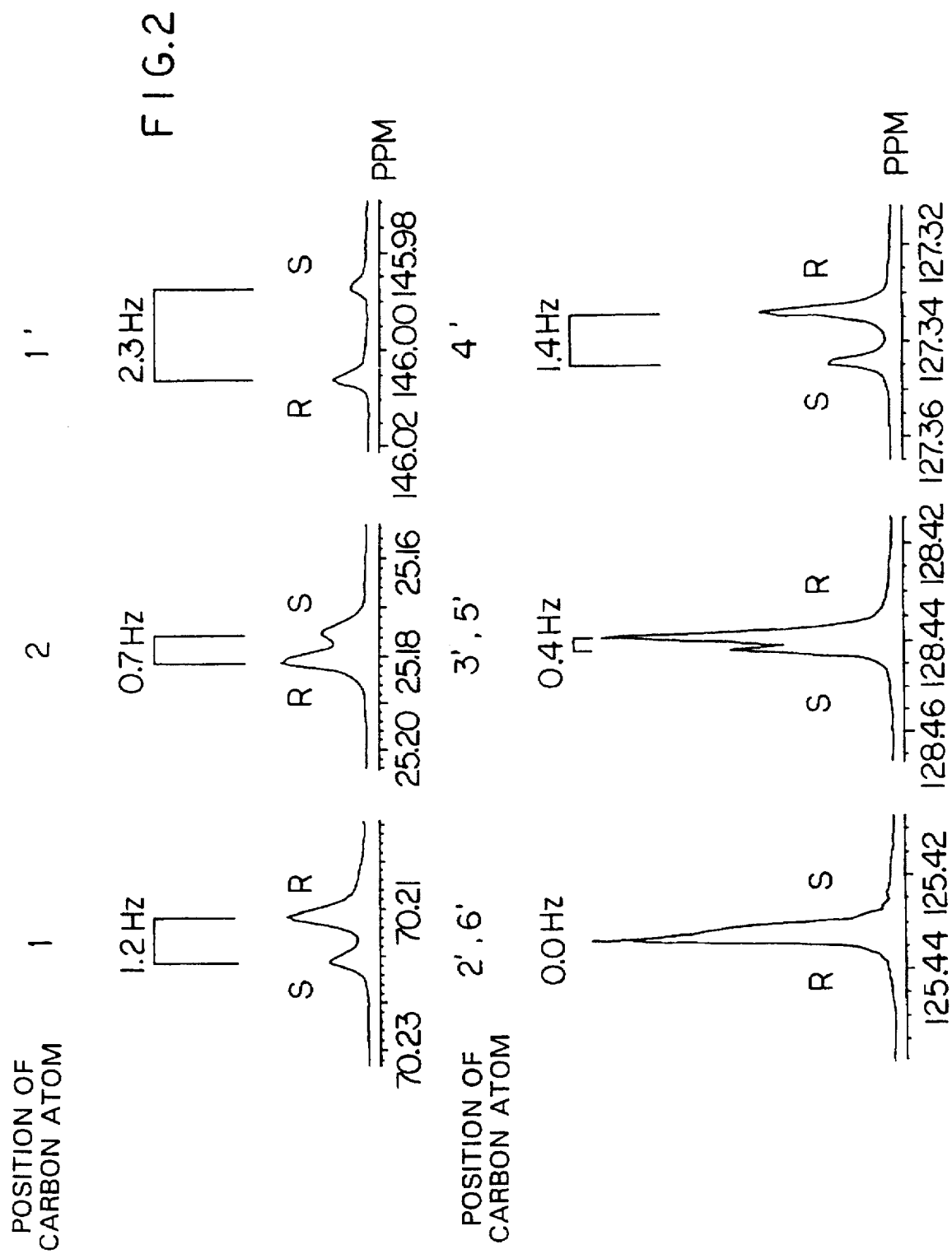
FIG. 2 is a drawing of the $^{13}$C-NMR spectra measured in the presence of the chiral shift reagent in Example 2.

The actual splittings of the $^{13}$C-NMR spectra are shown in FIG. 2.

Example 3

30 mg of racemic glutethimide represented by the following formula (11) was mixed with 100 mg of the chiral shift reagent (1). About 1.0 g of chloroform-d was added thereto. As a result of the $^{13}$C-NMR measurement at 35° C., similar to Example 1, the chemical shift given in Table 3 was obtained. For comparison, the chemical shift of glutethimide as measured in the absence of the chiral shift reagent (1) at 35° C. is given in the brackets.

TABLE 3

(11)

[Structure of glutethimide with numbered positions]

| Position of carbon atom | Chemical shift (ppm) |
|---|---|
| 2 | 175.05 [175.39] |
|   | 175.07 |
| 3 | 51.22 [51.14] |
| 4 | 29.33 [29.32] |
| 5 | 27.19 [27.19] |
|   | 27.22 |
| 6 | 172.12 [172.73] |
|   | 172.16 |
| 7 | 32.89 [32.90] |
|   | 32.91 |
| 8 | 9.11 [9.06] |
| 9 | 138.89 [138.92] |
|   | 138.95 |
| 10, 14 | 126.18 [126.21] |
| 11, 13 | 129.03 [129.00] |
| 12 | 127.60 [127.56] |
|   | 127.61 |

Figure 3A:
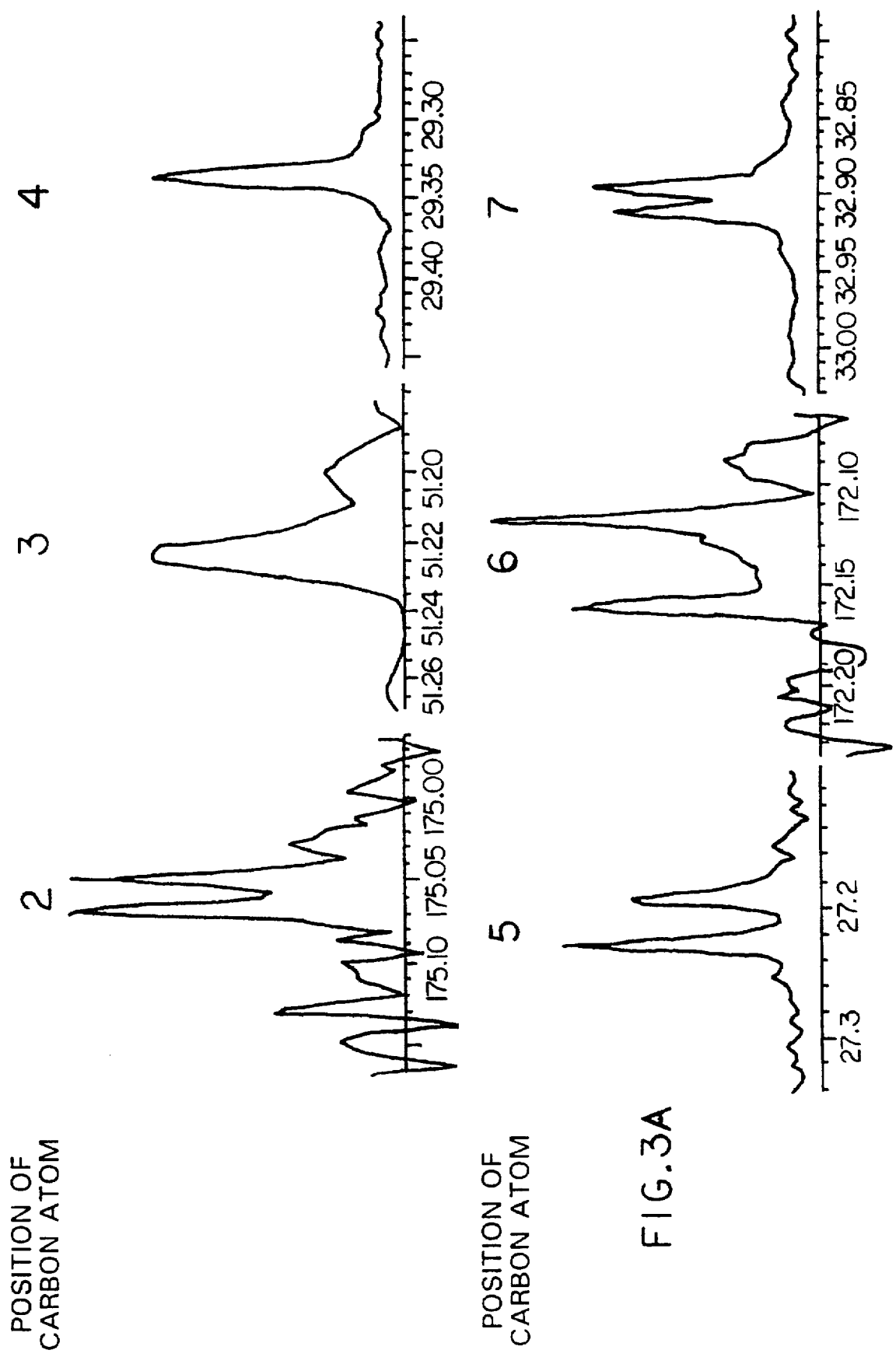
FIG. 3 is a drawing of the $^{13}$C-NMR spectra measured in the presence of the chiral shift reagent in Example 3.

The actual splittings of the $^{13}$C-NMR spectra are shown in FIG. 3.

Example 4

20 mg of cellulose tris(3,5-dichlorophenyl-carbamate) (hereinafter abbreviated to chiral shift reagent (2)) was added to 5.6 mg of racemic trans-stilbene oxide represented by the following formula (12), and about 8 mg of isopropyl alcohol was further added thereto, followed by dissolving them in about 1.0 ml (1.5 g) of chloroform-d. As a result of the $^1$H-NMR measurement at 22° C., the chemical shift given in Table 4 was obtained. For comparison, the chemical shift of trans-stilbene oxide as measured in the absence of the chiral shift reagent (2) at 22° C. is given in the brackets.

TABLE 4

(12)

[Structure of trans-stilbene oxide with H1 positions labeled]

| Position of hydrogen atom | Chemical shift (ppm) |
|---|---|
| 1 | 3.874 [3.870] 3.877 |

Figure 4:
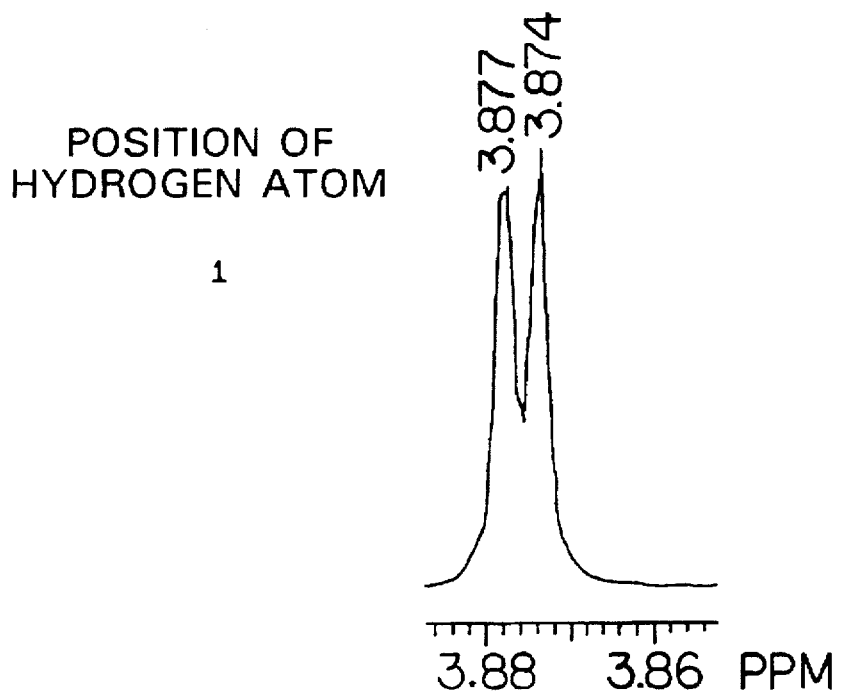
FIG. 4 is a drawing of the $^1$H-NMR spectrum measured in the presence of the chiral shift reagent in Example 4.

The actual ¹H-NMR spectrum is shown in FIG. 4.

Example 5

21 mg of tris(3,5-dimethylphenylcarbamoyl) maltooligosaccharide having a degree of polymerization of 6 (hereinafter abbreviated to chiral shift reagent (3)) was added to 5.0 mg of racemic trans-stilbene oxide represented by the above formula (12), followed by dissolving them in about 0.9 ml (1.35 g) of chloroform-d. As a result of the ¹H-NMR measurement at 22° C., the chemical shift given in Table 5 was obtained. For comparison, the chemical shift of trans-stilbene oxide as measured in the absence of the chiral shift reagent (3) at 22° C. is given in the brackets.

TABLE 5

| Position of hydrogen atom | Chemical shift (ppm) |
|---|---|
| 1 | 3.872 [3.870] 3.880 |

Figure 5:
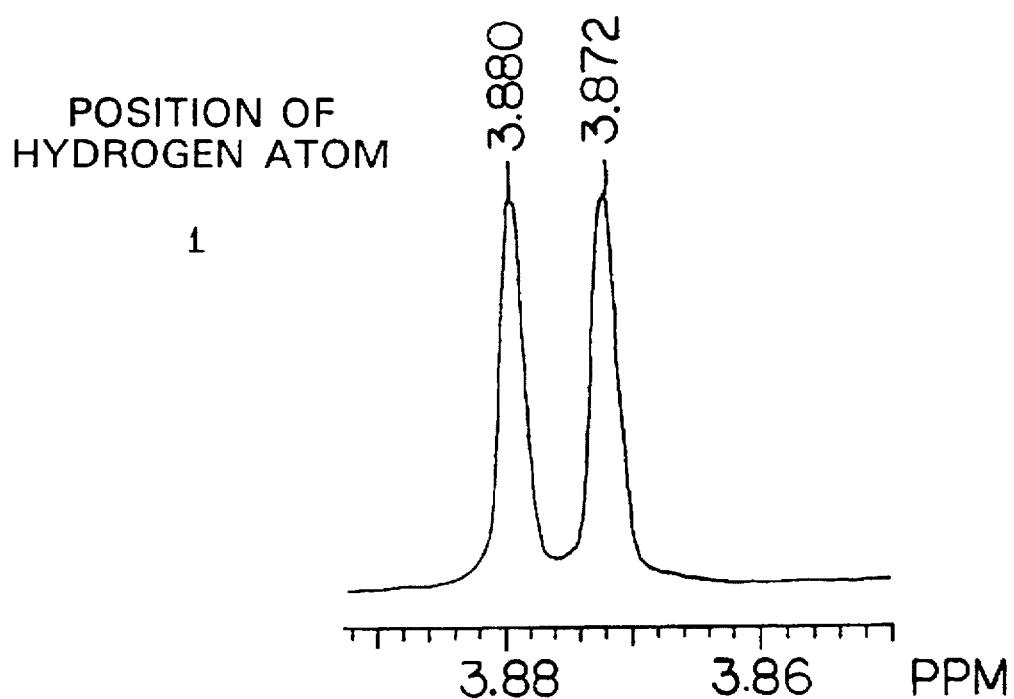
FIG. 5 is a drawing of the $^1$H-NMR spectrum measured in the presence of the chiral shift reagent in Example 5.
Figure 6:
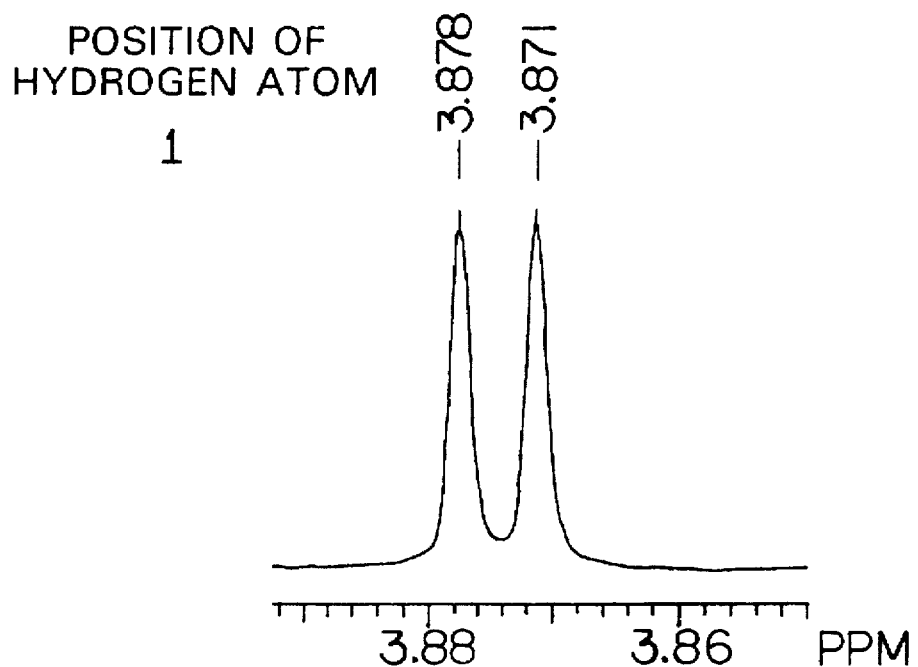
FIG. 6 is a drawing of the $^1$H-NMR spectrum measured in the presence of the chiral shift reagent in Example 6.

The actual ¹H-NMR spectrum is shown in FIG. 5.

Example 6

21 mg of tris(3,5-dimethylphenylcarbamoyl) maltooligosaccharlde having a degree of polymerization of 5 (hereinafter abbreviated to chiral shift reagent (4)) was added to 5.0 mg of racemic trans-stilbene oxide representd by the above formula (12), followed by dissolving them in about 0.9 ml (1.35 g) of chloroform-d. As a result of the ¹H-NMR measurement at 22° C., the chemical shift given in Table 6 was obtained. For comparison, the chemical shift of trans-stilbene oxide as measured in the absence of the chiral shift reagent (4) at 22° C. is given in the brackets.

TABLE 6

| Position of hydrogen atom | Chemical shift (ppm) |
|---|---|
| 1 | 3.871 [3.870] 3.878 |

Figure 8:
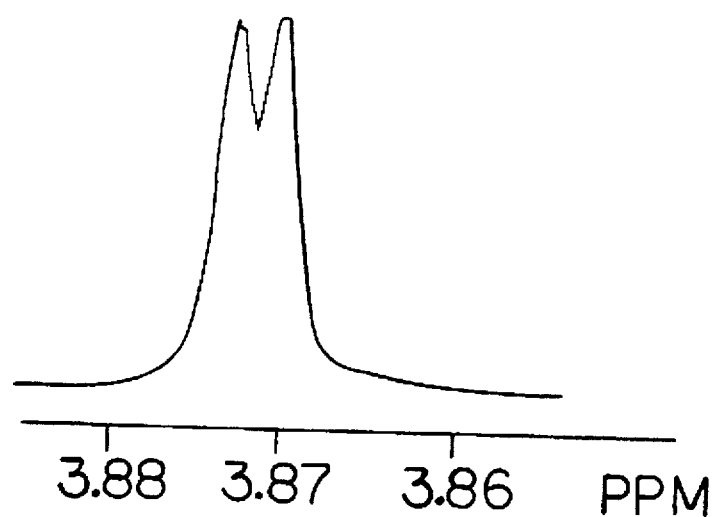
FIG. 8 is a drawing of the $^1$H-NMR spectrum measured in the presence of the chiral shift reagent in Example 8.

The actual ¹H-NMR spectrum is shown in FIG. 8.

Example 7

21 mg of tris(3,5-dimethylphenylcarbamoyl) maltooligosaccharide having a degree of polymerization of 3 (hereinafter abbreviated to chiral shift reagent (5)) was added to 5.0 mg of racemic trans-stilbene oxide represented by the above formula (12), followed by dissolving them in about 0.9 ml (1.85 g) of chloroform-d. As a result of the ¹H-NMR measurement at 22° C., the chemical shift given in Table 7 was obtained. For comparison, the chemical shift of trans-stilbene oxide as measured in the absence of the chiral shift reagent (5) at 22° C. is given in the brackets.

TABLE 7

| Position of hydrogen atom | Chemical shift (ppm) |
|---|---|
| 1 | 3.871 [3.870] 3.874 |

Figure 7:
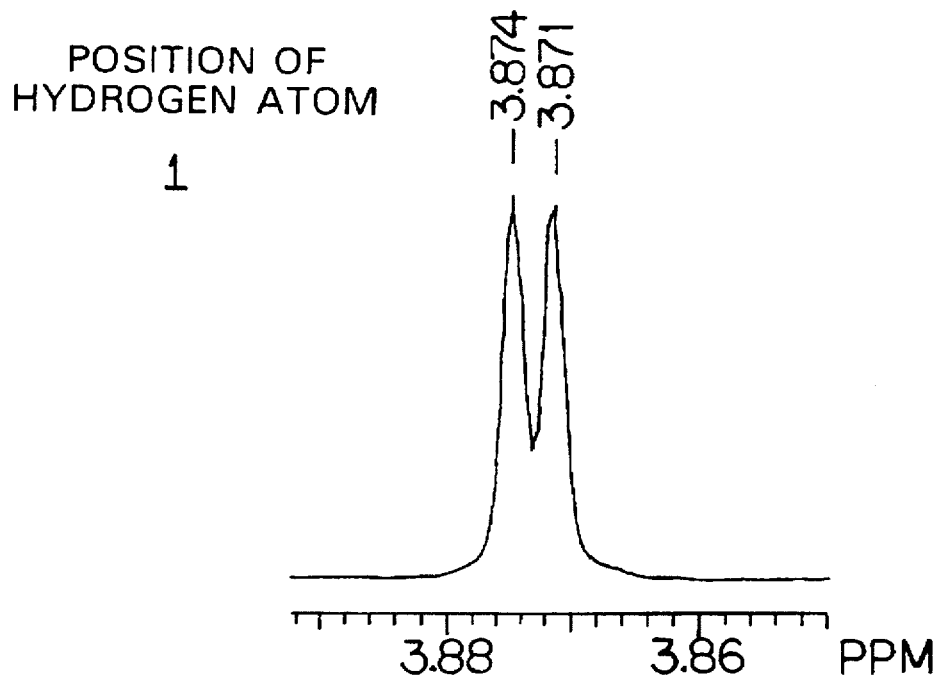
FIG. 7 is a drawing of the $^1$H-NMR spectrum measured in the presence of the chiral shift reagent in Example 7.

The actual ¹H-NMR spectrum is shown in FIG. 7.

Example 8

20 mg of cellulose tris(4-trimethylsilylphenylcarbamate) represented by the following formula (13) (hereinafter abbreviated to chiral shift reagent (6)) was added to 5.0 mg of racemic trans-stilbene oxide represented by the above formula (12), followed by dissolving them in about 1.0 ml (1.5 g) of chloroform-d. As a result of the ¹H-NMR measurement at 22° C., the chemical shift given in Table 8 was obtained. For comparison, the chemical shift of trans-stilbene oxide as measured in the absence of the chiral shift reagent (6) at 22° C. is given in the brackets.

TABLE 8

(13)

[Structure of cellulose tris(4-trimethylsilylphenylcarbamate) with three OCONH—C₆H₄—Si(CH₃)₃ groups]

| Position of hydrogen atom | Chemical shift (ppm) |
|---|---|
| 1 | 3.870 [3.871] 3.872 |

The actual ¹H-NMR spectrum is shown in FIG. 8.

We claim:

1. A method for analyzing the mixing ratio of optical isomers in an optical isomer mixture or the optical purity and absolute configuration of an optically active substance, said method comprising the steps of forming a resultant mixture containing the optical isomer mixture or the optically active substance, an organic solvent and a saccharide derivative chiral shift reagent and measuring an NMR spectrum of the resultant mixture to determine the mixing ratio of the optical isomers or the optical purity and absolute configuration of the optically active substance, the saccharide derivative being obtained by substituting at least one group selected from the groups consisting of an alkyl group, an aryl group, a nitro group, an alkenyl group, an acyl group and a carbamoyl group for at least one of the hydrogen atoms of the hydroxyl groups or amino groups of the saccharide.

2. The method according to claim 1, wherein the saccharide of the saccharide derivative is a monosaccharide, or a polysaccharide.

3. The method according to claim 2, wherein the polysaccharide has a degree of polymerization from 2–1000.

4. The method according to claim 3, wherein the degree of polymerization is from 2–8.

5. The method according to claim 3, wherein the degree of polymerization is from 2–500.

6. The method according to claim 1, wherein the solvent is chloroform.

7. The method according to claim 1, wherein the saccharide is a monosaccharide.

8. The method according to claim 1, wherein the saccharide is a polysaccharide.

9. The method according to claim 1, wherein the chiral shift reagent is selected from the group consisting of cellulose tris (p-methylbenzoate), cellulose tris(3,5-dichlorophenylcarbamate), tris(3,5-dimethylphenylcarbamoyl)maltooligosaccharide having a degree of polymerization of 5 or 6 and cellulose tris(4-trimethylsilylphenylcarbamate).

10. The method according to claim 1, wherein said saccharide is selected from the group consisting of allose, altrose, galactose, glucose, mannose, talose, xylose, sucrose, lactose, maltose, cellobiose, isomaltose, chitobiose, mannobiose, xylobiose, cyclodextrin, a cellooligosaccharide, a maltooligosaccharide; a β-1,4-glucan, an α-1,4-glucan, an α-1,6-glucan, a β-1,6-glucan, a β-1,3-glucan, an α-1,3-glucan, a β-1,2-glucan, a β-1,4-galactan, a β-1,4-mannan, an α-1,6-mannan, a β-1,2-fructan, a β-2,6-fructan, a β-1,6-glucan, a β-1,3-glucan, an α-1,3-glucan, a β-1,2-glucan, a β-1,4-galactan, a β-1,4-xylan, a β-1,3-xylan, a β-1,4-chitosan, a β-1,4-acetylchitosan, pullulan, agarose and alginic acid.

11. The method according to claim 10, wherein chloroform is the solvent.

12. A method for analyzing the mixing ratio of optical isomers in an optical isomer mixture or the optical purity and absolute configuration of an optically active substance, said method comprising the steps of forming a resultant mixture containing the optical isomer mixture or the optically active substance, an organic solvent and a saccharide derivative chiral shift reagent and measuring an NMR spectrum of the resultant mixture to determine the mixing ratio of the optical isomers or the optical purity and absolute configuration of the optically active substance, the saccharide derivative being obtained by reacting at least one of its hydroxyl or amino groups with an atomic group selected from among:

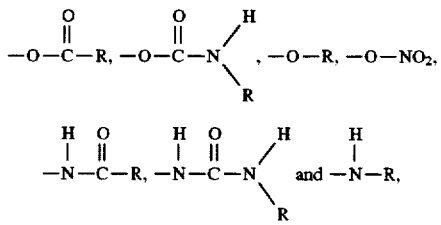

wherein R represents a group having from 1 to 30 carbon atoms, which may be unsaturated, or a phenyl group of the formula

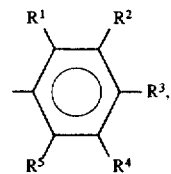

a hydrogen atom, an alkyl or alkylsilyl group having from 1 to 5 carbon atoms, a halogen atom or a nitro group.

13. The method according to claim 12, wherein said saccharide is selected from the group consisting of allose, altrose, galactose, glucose, mannose, talose, xylose, sucrose, lactose, maltose, cellobiose, isomaltose, chitobiose, mannobiose, xylobiose, cyclodextrin, a cellooligosaccharide, a maltooligosaccharide; a β-1,4-glucan, an α-1,4-glucan, an α-1,6-glucan, a β-1,6-glucan, a β-1,3-glucan, an α-1,3-glucan, a β-1,2-glucan, a β-1,4-galactan, a β-1,4-mannan, an α-1,6-mannan, a β-1,2-fructan, a β-2,6-fructan, a β-1,6-glucan, a β-1,3-glucan, an α-1,3-glucan, a β-1,2-glucan, a β-1,4-galactan, a β-1,4-xylan, a β-1,3-xylan, a β-1,4-chitosan, a β-1,4-acetylchitosan, pullulan, agarose and alginic acid.

14. The method according to claim 12, wherein chloroform is the solvent.

* * * * *

UNITED STATES PATENT AND TRADEMARK OFFICE
CERTIFICATE OF CORRECTION

PATENT NO. : 5 736 411
DATED : April 7, 1998
INVENTOR(S) : Yoshio OKAMOTO et al

It is certified that error appears in the above-indentified patent and that said Letters Patent is hereby corrected as shown below:

Column 10, line 27; AFTER third formula and
BEFORE "a hydrogen atom," insert
---wherein $R^1$, $R^2$, $R^3$, $R^4$ and $R^5$ is---.

Signed and Sealed this

Twenty-fifth Day of August, 1998

Attest:

BRUCE LEHMAN

Attesting Officer

Commissioner of Patents and Trademarks